United States Patent [19]
Javier, Jr. et al.

[11] Patent Number: 6,039,727
[45] Date of Patent: *Mar. 21, 2000

[54] CHANNEL FORMING DEVICE WITH PENETRATION LIMITER

[75] Inventors: Manuel A. Javier, Jr., Santa Clara; Stephen B. Pearce, Fremont; Randy J. Kesten, Mountain View; Sam G. Payne, Santa Clara; Kevin Gertner, Campbell, all of Calif.

[73] Assignee: Cardiogenesis Corporation, Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/584,957

[22] Filed: Jan. 11, 1996

Related U.S. Application Data

[63] Continuation-in-part of application No. 08/482,125, Jun. 7, 1995.

[51] Int. Cl.$^7$ .................................................. A61N 5/06
[52] U.S. Cl. .................................. 606/10; 606/7; 606/15
[58] Field of Search ............................................ 606/2–19

[56] References Cited

U.S. PATENT DOCUMENTS

| | | | |
|---|---|---|---|
| 3,982,541 | 9/1976 | L'Esperance, Jr. | 606/14 |
| 4,658,817 | 4/1987 | Hardy | 606/19 |
| 4,660,571 | 4/1987 | Hess et al. . | |
| 4,740,047 | 4/1988 | Abe et al. | 606/15 |
| 4,860,743 | 8/1989 | Abela . | |
| 4,862,887 | 9/1989 | Webb et al. | 606/7 |
| 4,890,898 | 1/1990 | Bentley et al. . | |
| 4,917,084 | 4/1990 | Sinofsky . | |
| 4,967,745 | 11/1990 | Hayes et al. . | |
| 4,985,029 | 1/1991 | Hoshino . | |
| 5,037,421 | 8/1991 | Boutacoff et al. | 606/15 |
| 5,093,877 | 3/1992 | Aita et al. . | |
| 5,125,926 | 6/1992 | Rudko et al. . | |
| 5,129,895 | 7/1992 | Vassiliadis et al. . | |
| 5,188,635 | 2/1993 | Radtke | 606/15 |
| 5,342,355 | 8/1994 | Long . | |
| 5,380,316 | 1/1995 | Aita et al. | 606/7 |
| 5,389,096 | 2/1995 | Aita et al. . | |
| 5,492,119 | 2/1996 | Abrams | 128/642 |
| 5,643,253 | 7/1997 | Baxter et al. | 606/17 |
| 5,666,970 | 9/1997 | Smith | 128/772 |
| 5,669,907 | 9/1997 | Platt, Jr. et al. | 606/48 |
| 5,672,170 | 9/1997 | Cho et al. | 606/12 |
| 5,673,704 | 10/1997 | Marchlinski et al. | 128/739 |
| 5,725,521 | 3/1998 | Mueller et al. | 606/7 |
| B1 5,147,354 | 10/1997 | Boutacoff et al. | 606/15 |

FOREIGN PATENT DOCUMENTS

| | | |
|---|---|---|
| 0 292 621 | 11/1988 | European Pat. Off. . |
| 0 622 051 A1 | 2/1994 | European Pat. Off. . |
| 0 797 957 | 3/1997 | European Pat. Off. . |
| 3443073 A1 | 5/1986 | Germany . |
| 39 11 796 A1 | 10/1996 | Germany . |
| 2 27 103 | 7/1990 | United Kingdom . |
| WO 94/20037 | 9/1994 | WIPO . |
| WO 97/13468 | 9/1996 | WIPO . |

OTHER PUBLICATIONS

Mirhoseini et al., Clinical Report: "Laser Myocardial Revascularization," Lasers in Surgery and Medicine 6:459–461 (1986).

(List continued on next page.)

*Primary Examiner*—David M. Shay
*Attorney, Agent, or Firm*—Heller Ehrman White & McAuliffe

[57] ABSTRACT

An laser device for forming channels within an outer wall of a patient's heart which has an elongated optical fiber, a lens or probe tip secured to the distal end of the optical fiber and means to limit the penetration of the probe tip or lens. Preferably, an outer support sleeve is secured to the proximal portion of the probe tip and a distal portion of the optical fiber proximal to the probe tip. In one preferred embodiment of the invention, a helical coil is disposed between the distal portion of the optical fiber and the proximal portion of the probe tip to ensure a better bond therebetween, particularly when the optical fiber has a lubricous fluoropolymer coating.

21 Claims, 3 Drawing Sheets

OTHER PUBLICATIONS

Mirhoseini et al., "Lasers in Cardiothoracic Surgery," in Lasers in General Surgery (Joffe, Editor), Williams and Wikins, 216–232 (1989).

Mirhoseini et al., "New Concepts in Revascularization of the Myocardium," A Thorac. Surg. 45:415–420 (Apr. 1988).

Walter et al., Europ. Surg. Res. 3:130–138 (1971).

Mirhoseini et al., "Myocardial Revascularization by Laser: A Clinical Report," Lasers in Surgery and Medicine 3:241–245 (1983).

Mirhoseini et al., "Revascularization of the Heart by Laser," Journal of Microsurgery 253–260 (Jun. 1981).

Mirhoseini, "Laser Applications in Thoracic and Cardiovascular Surgery," Medical Instrumentation, vol. 17, No. 6, 401–403 (Nov.–Dec. 1982).

Mirhoseini, "Laser Revascularization of the Heart," in New Frontiers in Laser Medicine and Surgery (Atsumi, Editor), ISBN Elsevier Science Publishing Co., 296–303 (1982).

Mirhoseini et al., "Transvenicular Revascularization by Laser," Lasers in Surgery and Medicine 2:187–198 (1982).

CHANNEL FORMING DEVICE WITH PENETRATION LIMITER

RELATED APPLICATIONS

This application is a continuation-in-part of copending application Ser. No. 08/482,125, filed on Jun. 7, 1995, which is incorporated herein by reference in its entirety.

BACKGROUND OF THE INVENTION

This invention is directed to the formation of one or more channels into the wall of a patient's heart which may be used to increase blood flow to heart tissue experiencing ischemic conditions, for the delivery of therapeutic or diagnostic agents to various locations in the patient's heart or for a variety of other utilities.

The formation of a channel in a patient's ventricular wall to increase the blood to flow to a patient's heart tissue is called trans myocardial revascularization. The first clinical trials of the trans myocardial revascularization process were performed by Mirhoseini et al. See for example the discussions in *Lasers in General Surgery* (Williams & Wilkins; 1989), pp 216–223. Other early disclosures of this procedure is found in an article by Okada et al. in Kobe J. Med. Sci 32, 151–161, October 1986 and U.S. Pat. No. 4,658,817 (Hardy). These early references describe intraoperative revascularization procedures which require an opening in the chest wall and include formation of the channels through the epicardium.

Copending application Ser. No. 08/361,787, filed Dec. 20, 1994 (Aita et al.), which is incorporated herein in its entirety, describes a system for trans myocardial revascularization which is introduced through the chest wall. In U.S. Pat. No. 5,389,096 (Aita et al.) a percutaneous method is described for forming a channel in a patient's ventricular wall wherein an optical fiber device is advanced through a peripheral artery such as the femoral artery, through the aorta into the patient's left ventricle. Within the left ventricle, the distal end of the optical fiber device is directed toward a desired location on the patient's endocardium and urged against the endocardial surface while a laser beam is emitted from its distal end to form the channel. The depth of penetration of the distal end of the laser device is affected by the force applied by the distal end to the tissue into which the channel is being formed. Because of the nature of the environment, i.e. fluid currents, the moving heart surface and the uneven surface of the patient's endocardium, controlling the force applied to the endocardial tissue by the end of the laser device can be quite difficult. Complete penetration through the ventricular wall from within the ventricular chamber is not desirable.

The present invention minimizes the difficulties with these prior channel forming devices.

SUMMARY OF THE INVENTION

The present invention is directed to an improved device for forming a channel in a ventricular wall of a patient's heart and particularly in the free-wall defining in part the left ventricle of the patient's heart.

The channel forming device of the invention generally includes an elongated shaft with a proximal and distal shaft sections. A means to form a channel in the ventricular wall of the is provided on the distal shaft section and a means to limit the depth of penetration of the distal shaft section into heart tissue during the formation of the channel therein. The means to limit the depth of penetration is preferably at least one radial projection on the distal shaft section spaced proximally from the means to form the channel on the distal shaft section.

In one presently preferred embodiment, the invention includes an elongated optical fiber having a proximal end and a distal end and a distal probe tip secured to the distal extremity of the optical fiber. The laser device is provided with one or more radially extending projections spaced from the distal end of the device which acts as a stop to limit the penetration or forward motion of the operative end of the device into the ventricular wall during channel formation, which in turns controls the depth of the channel into the ventricular wall. The means to limit the penetration into the ventricular wall may be a plurality of arms, preferably four, which fold back when the channel forming device is advanced within a guiding or delivery catheter to the ventricular chamber, but which expand outwardly when the distal section exits the distal end of the guiding or delivery catheter within the chamber. Another means for limiting the depth of penetration into the ventricular wall is to provide a radially projecting shoulder on the exterior of the distal shaft section proximal to the channel forming means. In each of these means the stopping surface is spaced from the distal end of the probe tip the desired penetration distance for the distal tip of the device. By providing the means to control the depth of penetration, there is no need for concern about the pressure applied by the physician to the channel forming device affecting the depth of penetration which may lead to the complete penetration of the ventricular wall. A wide variety of means can be used to prevent such penetration.

The means to form a revascularization channel may be an electrical or radio frequency ablation means, a water jet means, a rotating mechanical means, and ultrasonic energy ablation means or other suitable non-laser means. The means should be chosen in order to provide efficient tissue removal with good control over channel formation.

The presently preferred channel forming device is an elongated optical fiber with a distal probe tip on the distal end of the optical fiber to control the emission laser radiation therefrom. The distal probe tip preferably has an interior chamber into which the distal extremity of the optical fiber extends and an outer support member or sleeve is secured to the proximal portion of the probe tip and a distal portion of the optical fiber extending out the proximal end of the probe tip to ensure the integrity of the probe tip and optical fiber during the channel forming procedure. The outer support sleeve may be shrunk fit onto the probe tip or it may be bonded by a suitable adhesive. Further details of this construction can be found in copending application Ser. No. 08/482,125, filed on Jun. 7, 1995.

In a presently preferred device for forming channels in the ventricular wall from within the ventricular chamber which is percutaneously introduced into the patient's vascular system, the probe tip length is about 3 to about 20 mm and the length of the portion of the probe tip which extends out the distal end of the outer support member is about 1 to about 5 mm. Generally, at least about 1 mm of the proximal portion of the probe tip, preferably at least about 2 mm thereof, is secured by the outer support member to ensure holding the probe tip in the case of a fractured probe tip. The proximal portion of the outer support member secured to the distal end of the optical fiber should be at least about the same length as described above for the distal portion, although generally it will be longer. For an interoperative device which is designed to form channels from the exterior of the patient's heart the dimensions may be significantly larger than those set forth above for a percutaneous device.

An adapter is provided on the proximal end of the device which is configured to connect the proximal end of the optical fiber in an optical transmission relationship with a laser source.

While forming a passageway through the wall of the patient's heart for the purpose of revascularization is of significant importance, the passageway formed into the heart wall may be used for other purposes. For example, therapeutic or diagnostic agents may be introduced into the channel for delivery to the patient's endocardium or myocardium. The therapeutic or diagnostic agent may be incorporated into a biocompatible matrix deposited within the channel for delivery or release over an extended period.

These and other advantages of the invention will become more apparent from the following detailed description of the invention, when taken in conjunction with the accompanying exemplary drawings.

DETAILED DESCRIPTION OF THE INVENTION

Figure 1:
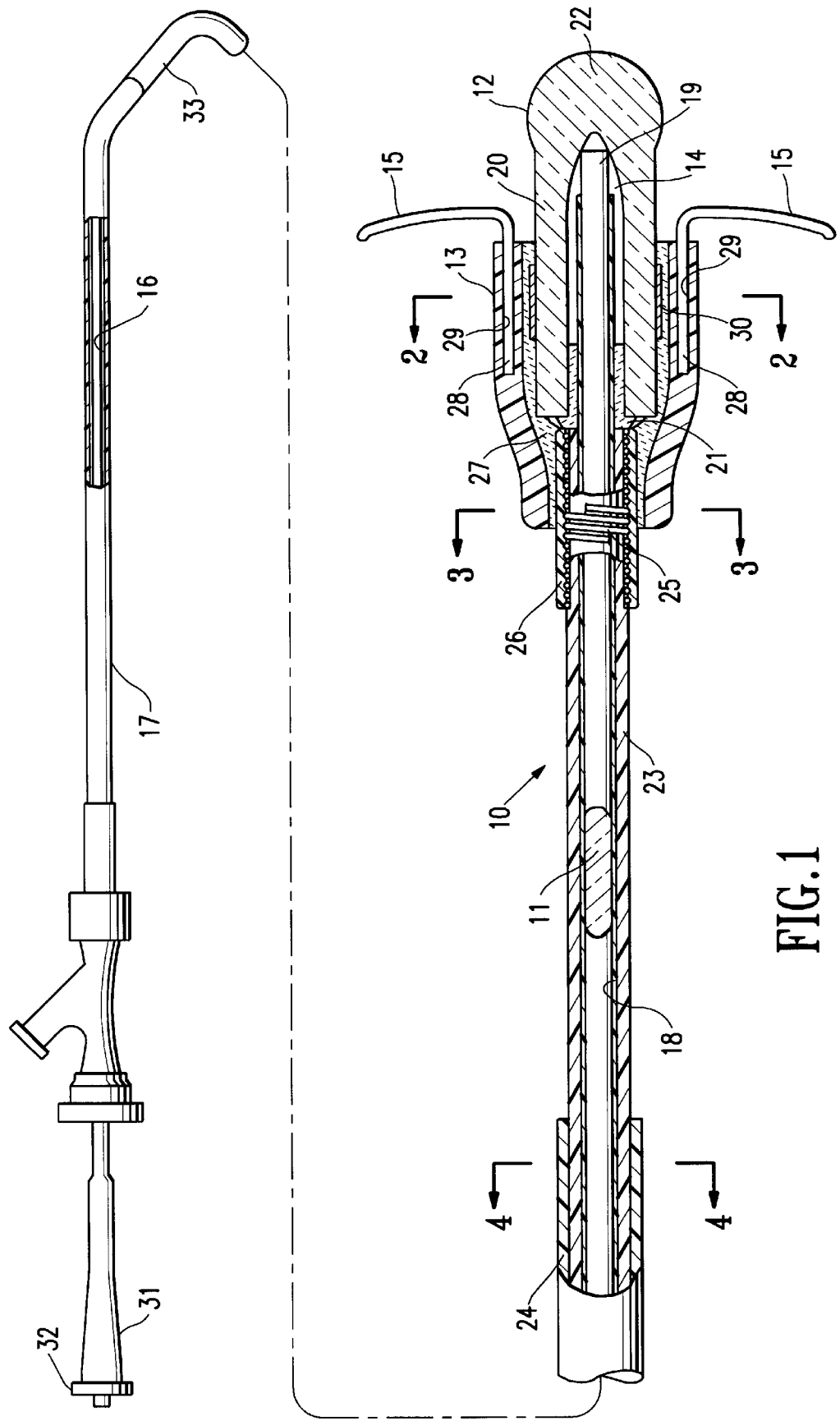
FIG. 1 is an elevational view, partially in section, of a channel forming device embodying features of the present invention.
Figure 2:
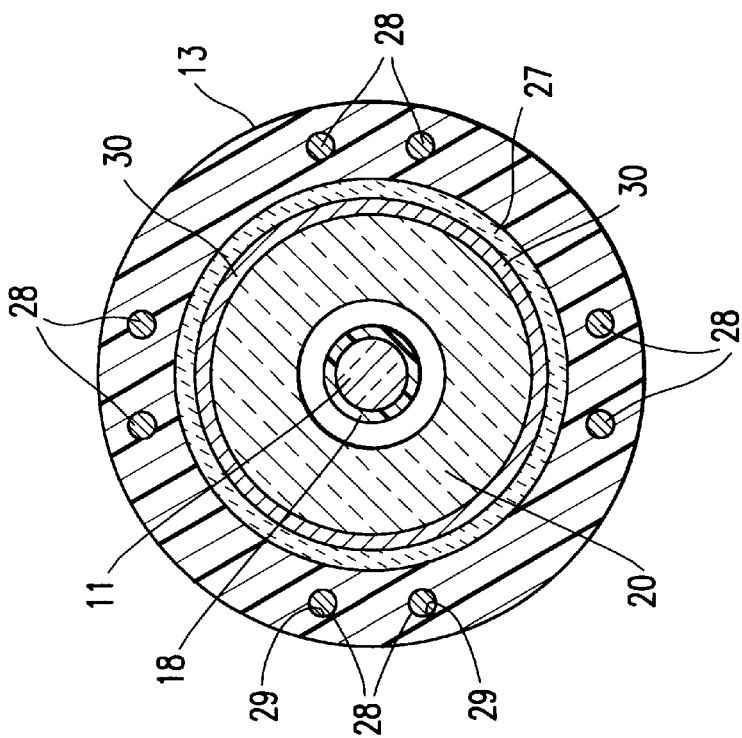
FIG. 2 is a transverse cross-sectional view of the channel forming device shown in FIG. 1, taken along the lines 2—2.
Figure 3:
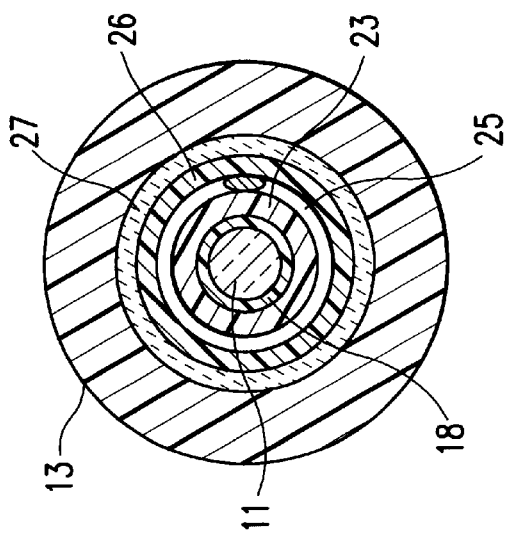
FIG. 3 is a transverse cross-sectional view of the channel forming device shown in FIG. 1, taken along the lines 3—3.
Figure 4:
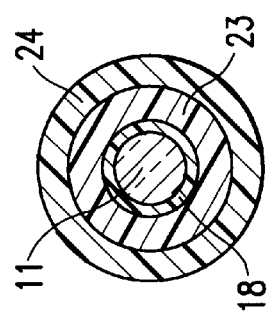
FIG. 4 is a transverse cross-sectional view of the channel forming device shown in FIG. 1, taken along the lines 4—4.

In FIGS. 1–4 a channel forming device 10 is shown which embodies features of the invention. The device 10 includes an elongated optical fiber 11, an elongated probe tip 12 disposed about and secured to the distal extremity of the optical fiber, and an outer tubular support member or sleeve 13 secured to the exterior of the proximal extremity of the probe 12 and a distal portion of the optical fiber which is not disposed in the interior chamber 14 of the probe 12. A plurality of radially extending arms 15 are provided proximal to the distal end of the probe tip to limit the penetration of the probe tip into the patient's ventricular wall. The channel forming device 10 is slidably disposed within the inner lumen 16 of guiding catheter 17. A positioning catheter (not shown) may be disposed between channel forming device 10 and the guiding catheter 17 which can facilitate closer placement of the probe tip 12 onto the endocardium of the ventricular wall as described in copending application Ser. No. 08/438,743, filed on May 10, 1995. This latter application is incorporated herein in its entirety by reference.

The exterior of the optical fiber 11 is provided with a fluoropolymeric cladding 18 along its length except for a distal portion 19 which extends into the distal end of the interior chamber 14 of the probe tip 12.

The elongated probe tip 12 has a cylindrical body 20 which is bonded to the distal end of the optical fiber 11 by adhesive 21. The probe tip 12 has a distal end 22 which acts as a lens to control laser energy emitted from the distal end of the optical fiber to a location immediately distal to the lens to ensure formation a channel of a desired size in the ventricular wall. A fluoropolymer buffer 23 is disposed about the optical fiber 11 proximal to the body of adhesive 21 and extends proximally along essentially the remainder of the optical fiber. An outer jacket 24 is disposed about the fluoropolymer buffer 23 along most of its length, and terminates about 10 cm from the proximal end of the outer tubular support member 13. A helical coil 25 formed of high strength material such as stainless steel, NITINOL and the like is disposed between the fluoropolymer buffer 23 and the proximal end of the outer tubular support member 13 and has a jacket 26 formed of suitable plastic material such al polyethylene terephthalate (PET). The coil 25 and jacket 26 together facilitate an effective bond between the fluoropolymer buffer 23 and the outer tubular support member 13. Adhesive 27 bonds the outer tubular support member 13 to the coil jacket 26.

Figure 6:
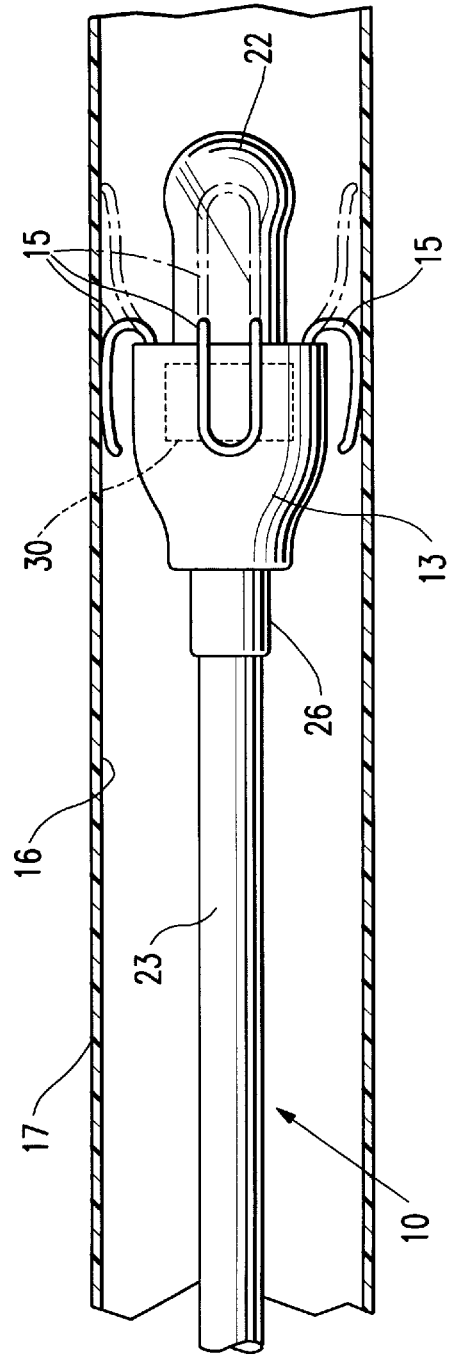
FIG. 6 is an elevational view of the device shown in FIG. 1 disposed within a guiding catheter.

The radially extending arms 15 are U-shaped flexible wire members with the free ends 28 embedded within the outer tubular support member 13. Preferably, the outer tubular support member 13 is provided with lumens 29 which receive the free ends 26 of the arms 15 and are secured therein by a suitable adhesive (not shown). Other means may be utilized to secure the free ends 28 of the arms 15 between the probe tip 12 and the exterior of the outer tubular support member 13. When expanded radially, the arms 15 act to limit the penetration of the probe tip 12 into the channel as it is being formed in the ventricular wall and thus controls the depth of the channel formed. As is shown in FIG. 6, the arms 15 are folded backwardly while the probe tip 12 of optical fiber device 10 is disposed within the inner lumen 16 of the guiding catheter 17. Alternatively, they may be folded forwardly as shown in phantom in FIG. 6. Preferably, the arms 15 are formed of a NiTi alloy having superelastic characteristics at body temperature to facilitate the folding thereof within the guiding catheter 17 and the radial expansion thereof once the probe tip 12 extends out of the distal end of the guiding catheter. Folding the arms 15 causes the stress induced transformation of the austenite phase of the NiTi alloy in the bent portions to the martensite phase and release of the arms to allow for their radial expansion causes the transformation of the martensite phase back to the austenite phase.

A radiopaque band 30 may be secured to the exterior of the cylindrical body 20 by the adhesive 27 to facilitate the fluoroscopic observation of the probe tip 12 during the procedure. The band may be formed of a wide variety of metallic components including gold, platinum iridium and the like.

The proximal end of the device 10 is provided with a connector 31 which has a rotatable, internally threaded collar 32 which facilitates an optical connection of the proximal end of the optical fiber 11 with a source of laser energy.

The distal end 33 of the guiding catheter 17 is preferably formed into a desired shape which directs the distal extremity of the optical fiber 11 and the probe tip 12 onto a desired location on the surface of the free ventricular wall of the patient's heart. If a positioning catheter is employed, its distal end may likewise be formed with a desirable shape to facilitate directing the probe tip to the desired location.

The various components of the device 10 may be formed of a wide variety of conventional materials used in the construction of intravascular catheters and other intracorporeal devices. The contemplated materials of construction and the sources thereof for one presently preferred embodiment are provided in the following table.

| COMPONENT | MATERIAL | SUPPLIER |
|---|---|---|
| Proximal Optical Connector | Various | Amphenol Corporation Lisle, IL and Spectran[1] Specialty Optics, Co. Avon, CT |
| Jacket (24) | Pebax 7233 tubing with 3% $TiO_2$ | North American Infinity Extrusions and Engineering, Inc. Santa Clara, CA 95054 |
| Tubular Support Member (13) | Nylon 12, ⅛" | Guidant Corporation 3200 Lakeside Dr. Santa Clara, CA 95052 |
| UV-Cured Adhesive (20) | Urethane Oligomer (197-M) Acrylate | Dymax Corp. Torrington, CT |
| PET Shrink Tubing (26) | Polyethylene Terephthalate | Advanced Polymers, Inc. Salem, NH |
| Probe (12) | Fused Quartz | Polymicro Technologies, Inc. Phoenix, AZ |
| Optical Fiber Buffer (23) | Tefzel ® | Spectran[1] Specialty Optic Co. Avon, CT |
| Optical Fiber Cladding (18) | Proprietary Flouropolymer Acrylate | Spectran[1] Specialty Optic Co. Avon, CT |
| Optical Fiber (11) | Fused Silica (Low OH⁻) | Spectran[1] Specialty Optic Co. Avon, CT |

The overall length of a channel forming device in accordance with the present invention is about 200 to about 400 cm with a typical value being about 350 cm. The actual length being determined by the location of the source of laser energy. The operative distal portion of the device, i.e. the portion which is inserted into the patient is about 10 to about 60 cm in length. The probe tip for percutaneous use is about 3 to about 10 mm in length with the length of the exposed distal portion which extends out of the tubular support member being about 1 to about 5 mm, preferably about 2 to about 4 mm. For intraoperative use the probe tip should be about 5 to about 50 mm in length with about 2 to about 30 mm, preferably about 10 to about 25 mm, extending out of the tubular support member. The outer diameter of the probe tip is about 1 to about 3 mm, preferably about 1.5 to about 2 mm, and is measured at the widest portion of the bulbous tip which forms the lens. The outer diameter of the coating or jacket on the probe tip is essentially the same as the bulbous tip. The length of the outer tubular support member is about 0.3 to about 40 cm, preferably about 0.5 to about 30 cm and the length of the radial extension of the arms 15 is about 0.5 to about 2 mm.

Figure 7:
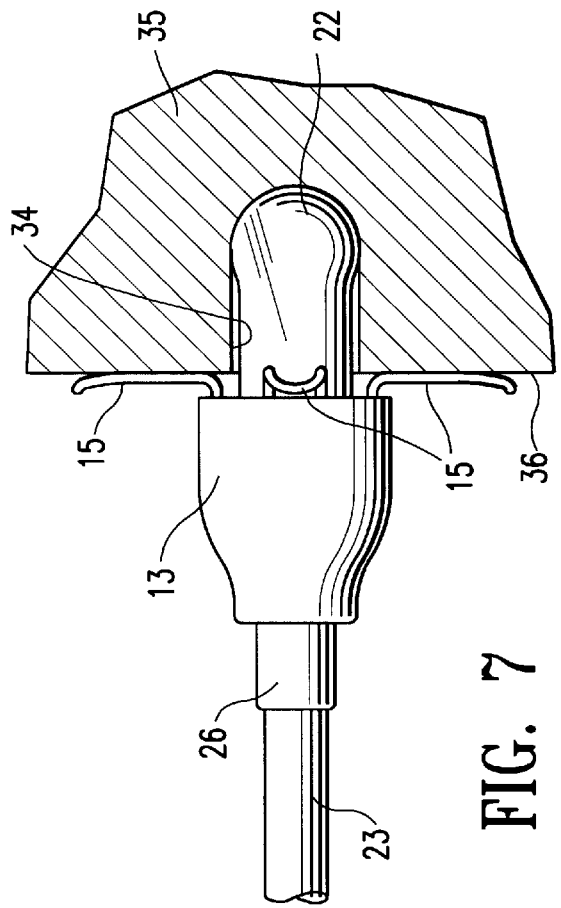
FIG. 7 is an elevational view of the device shown in FIG. 1 disposed within a channel of a ventricular wall shown in section.
Figure 5:
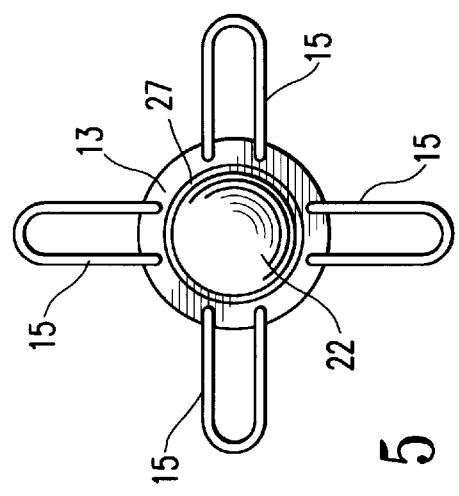
FIG. 5 is an end view of the device shown in FIG. 1.

FIG. 7 illustrates the use of the channel forming device wherein the probe tip 12 is disposed within the channel 34 in the ventricular wall 35. The arms 15 rest upon the ventricular surface 36 limiting the penetration of the probe tip 12.

Although individual features of embodiments of the invention may be shown in some of the drawings and not in others, those skilled in the art will recognize that individual features of one embodiment of the invention can be combined with any or all the features of another embodiment. Moreover, while the present invention has been described herein primarily in terms of a laser based channel forming device which is percutaneously introduced into the patient's vascular system and then advanced therein until the operative end is disposed within a chamber of the patient's heart, those skilled in the art will recognize that the device of the invention may be utilized in an interoperative procedure where the device is introduced into the patient's chest cavity and the channel is formed through the patient's epicardium. In this instance, however, the dimensions of the device may have to be changed to accommodate the slightly different delivery system. Additionally, a variety of non-laser channel forming devices may be utilized. See for example those non-laser devices described in co-pending application Ser. No. 08/517,499, filed on Aug. 9, 1995, which is incorporated herein in its entirety. Other modifications and improvements may be made to the invention without departing from the scope thereof.

What is claimed is:

1. A device for forming a channel into a ventricular wall of a patient's heart comprising:

a) an elongated shaft having a proximal shaft section, a distal shaft section and a distal end;

b) at least one optical probe member disposed on the distal end of the shaft which has a proximal end, a distal end, and an energy emitting surface disposed on the distal end, said energy emitting surface configured for engaging the ventricular wall of the patient's heart, emitting laser energy, forming a channel therein, and mechanically penetrating said channel; and c) at least one radially expandable member secured to the optical probe member having a penetration limiting surface when in an unconstricted state, the entire penetration limiting surface being spaced proximally from the energy emitting surface of the optical probe member and the penetration limiting surface being configured to limit penetration of the energy emitting surface of the optical probe member into the ventricular wall during formation of the channel therein to a distance substantially equal to a distance between the energy emitting surface and the penetration limiting surface.

2. The device of claim 1 wherein the expandable member is substantially perpendicular to a longitudinal axis of the elongated shaft and optical probe member when in an unconstricted state.

3. The device of claim 2 wherein the expandable member is an outwardly extending arm.

4. The device of claim 3 wherein the outwardly extending arm is foldable over the exterior of the distal shaft section to facilitate advancement of the device through an inner lumen of a delivery catheter.

5. A device for forming a channel into a wall of a patient's heart comprising:

a) an optical probe member having an open proximal end, a distal end, a lens member on the distal end for controlling emitting laser radiation and an interior chamber;

b) an elongated optical fiber having proximal and distal ends, a distal extremity which extends through the open proximal end of the probe member into the interior chamber thereof with the distal end of the optical fiber being in an optical transmitting relationship with the lens member on distal end of the optical probe member; and c) at least one radially expandable member which is self expanding from a constricted configuration and which is secured to the optical probe member and which has a penetration limiting surface in an expanded unconstricted state, the entire penetration limiting surface being spaced proximally from the lens member, and the penetration limiting surface being configured to limit mechanical penetration of the lens member into heart tissue to a distance substantially equal to a distance between the lens member and the penetration limiting surface.

6. The device of claim 5 wherein the radially expandable member is configured in a loop having an outer end and the outer end extends radially outward from the optical probe member to a radial transverse distance of at least 0.5 mm from an outer surface of the optical probe member.

7. The device of claim 5 wherein a tubular support member is disposed about and secured to a proximal portion of the optical probe member and a distal portion of the optical fiber which is not disposed within the interior chamber of the optical probe member.

8. The device of claim 6 wherein the optical probe member is about 3 to about 10 mm in length.

9. The device of claim 6 wherein the optical probe member is about 5 to about 50 mm in length.

10. The device of claim 6 wherein the length of the optical probe member extending out of the tubular support member is about 1 to about 30 mm.

11. The device of claim 6 wherein the length of the optical probe member extending out of the tubular support member is about 2 to about 25 mm.

12. The device of claim 6 wherein the optical fiber is provided with a fluoropolymer cladding over essentially its entire length excluding its distal tip which is essentially free of such cladding.

13. The device of claim 12 wherein a helical coil is disposed between the flouropolymer cladding on the optical fiber and the proximal end of the tubular support member.

14. The device of claim 13 wherein the helical coil is provided with a polymer jacket to facilitate securing the outer tubular member to the optical fiber 11.

15. A device for ablating tissue in a wall of a patient's heart comprising:
   a) an elongated shaft having a proximal shaft section, a distal shaft section and a distal end;
   b) a tissue ablating member which has a proximal end and a distal end and which is disposed upon the distal end of the elongated shaft, the distal end of the tissue ablating member being adapted for engaging the wall of the patient's heart and ablating tissue therein; and
   c) at least one radially expandable member which is made of a loop of superelastic alloy secured at free ends of the loop to the device and which has a penetration limiting surface, the entire penetration limiting surface being spaced proximally from the distal end of the tissue ablating member, said radially expanding member being self expanding from a constricted configuration, which causes a stress induced martensite phase in at least a portion of the radially expandable member, to limit penetration of the distal end of the tissue ablating member into the wall of a patient's heart during ablation of tissue therein to a distance substantially equal to a distance between the distal end of the tissue ablating member and the penetration limiting surface.

16. The device of claim 15 wherein the tissue ablating member is configured to form a channel into the wall of a patient's heart.

17. The device of claim 15 wherein the tissue ablating member is comprised of an optical probe optically coupled to a laser energy source.

18. The device of claim 15 wherein the tissue ablating member is comprised of an ultrasonic energy probe energetically coupled to an ultrasonic energy source.

19. The device of claim 15 wherein the tissue ablating member is comprised of a radio frequency probe electromagnetically coupled to a radio frequency energy source.

20. The device of claim 15 wherein the tissue ablating member is comprised of a water jet tissue removal probe.

21. The device of claim 15 wherein the tissue ablating member is comprised of a rotating mechanical tissue removal probe.

* * * * *